United States Patent
Nace

(10) Patent No.: US 8,388,564 B2
(45) Date of Patent: Mar. 5, 2013

(54) HYPEREXTENSION KNEE BRACE

(76) Inventor: Richard A. Nace, San Jose (CR)

(*) Notice: Subject to any disclaimer, the term of this patent is extended or adjusted under 35 U.S.C. 154(b) by 0 days.

(21) Appl. No.: 13/291,910

(22) Filed: Nov. 8, 2011

(65) Prior Publication Data

US 2012/0123308 A1     May 17, 2012

Related U.S. Application Data

(60) Provisional application No. 61/410,974, filed on Nov. 8, 2010.

(51) Int. Cl.
    *A61F 5/00*     (2006.01)

(52) U.S. Cl. ............................................. 602/13; 602/26

(58) Field of Classification Search .................... 602/13, 602/16, 23, 26, 27; 128/882, DIG. 20; 5/621–624, 5/636, 644–646, 648
See application file for complete search history.

(56) References Cited

U.S. PATENT DOCUMENTS

| | | | | |
|---|---|---|---|---|
| 5,360,394 A * | 11/1994 | Christensen | .................... | 602/26 |
| 5,458,565 A * | 10/1995 | Tillinghast et al. | ............. | 602/26 |
| 5,520,622 A * | 5/1996 | Bastyr et al. | .................... | 602/16 |
| 5,527,268 A * | 6/1996 | Gildersleeve et al. | .......... | 602/26 |
| 5,542,911 A * | 8/1996 | Cassford et al. | ................ | 602/26 |
| 5,865,166 A * | 2/1999 | Fitzpatrick et al. | ........ | 128/117.1 |

* cited by examiner

*Primary Examiner* — Michael A. Brown
(74) *Attorney, Agent, or Firm* — Larson & Larson, P.A.; Frank Liebenow; Justin P. Miller

(57) ABSTRACT

A knee brace for treating hyperextension in a patient's knee. The knee brace includes two lateral uprights and a back support positioned horizontally to and generally at a middle portion of the lateral uprights. The lateral uprights and the back support define an integral frame. A plurality of straps includes a thigh, shin and patella strap connected at opposed ends to the frame for securing the brace to the patient. A plurality of cushion pads is disposed along inner surfaces of the lateral uprights and the thigh and shin straps for providing comfort and for mitigating brace migration. An inflatable air bladder is located on an inner surface of the back support for positioning behind the knee. The air bladder has an inflation tube for increasing or decreasing the air volume within the air bladder to affect a range of motion for the patient's knee.

13 Claims, 7 Drawing Sheets

HYPEREXTENSION KNEE BRACE

PRIOR APPLICATIONS

This application is a continuation-in-part of provisional patent application No. 61/410,974, filed Nov. 8, 2010, still pending.

FIELD OF THE INVENTION

The present invention relates to a knee orthosis device used in the correction and treatment of genu recurvatum. More particularly, it refers to a knee brace for correcting hyperextension moment of the knee joint and preventing genu recurvatum displacement of the knee during gait.

BACKGROUND OF THE INVENTION

Orthotic devices and appliances commonly referred to as "orthotics," are known in the prior art and have been utilized for many years by doctors, orthotists, physical therapists and occupational therapists. They are primarily used to protect an injured or surgically repaired ankle or knee joint or a weakened joint caused by neurological disability or physiological deformity.

One such deformity is known as genu recurvatum of the knee. Genu recurvatum is a sustained posteriorly directed hyperextension moment of the knee joint (i.e., the knee bends backwards) occurring throughout the loading period of gait, from initial contact through forward progression. The posterior deviation of the knee joint (specifically in the tibiofemoral joint) disrupts normal gait and can negatively affect step length, stride length, gait velocity, walking cadence, increased lateral trunk displacement, and increased energy consumption while walking. If untreated, genu recurvatum can lead to significant knee joint deformities, which negatively affects walking ability and can predispose a patient to serious knee injury, knee pain and even cause knee osteoarthritis. Normal range of motion (ROM) of the knee joint is from 0 to 135 degrees in an adult. Full knee extension should be 0 degrees. In genu recurvatum normal extension is increased past 0 degrees.

The Swedish Knee Cage designed in the mid-1960s was the initial prefabricated commercially available knee brace to help control genu recurvatum. A typical Swedish Knee Cage brace design is a rigid "cage-like" unit that includes two upper lateral and medial uprights, two lower lateral and medial uprights and a generally U-shaped fixed posterior padded metal bar extending behind the knee. Also included are straps or cuffs and straps that secure the cage brace to the thigh and shin of a patient's leg. The padded metal bar is suppose to "block" or inhibit posterior movement of the knee joint. The metal "hyperextension stop" bar in some models is adjustable so that the brace fitter can stop the hyperextension of the knee at various positions depending on patient needs. Swedish Knee Cage designs all work as a physical block with a bar directly behind the knee to prevent movement backwards of the knee joint to simply control posterior movement of the knee. A typical Swedish Cage Knee Brace can be seen in U.S. Pat. No. 5,207,637 to Janke et al.

The Swedish Knee Cage design is essentially a static-design brace since the rigid component positioned behind the knee joint simply "blocks" the posterior movement of the knee joint. During the loading phase of gait, the knee joint of a genu recurvatum patient will move past neutral (i.e., straight leg) with the knee hyper-extending backwards away from the midline of the body. The rigid block positioned behind the knee stops posterior movement of the knee joint. The patient at the hyperextension moment of the "block" loses all inertia and must push off of the "block" to move forward. This creates a "halting" gait, wherein more time is spent on the affected leg with weight bearing than the unaffected leg during gait. This disrupts a normal gait pattern, requires significant additional energy to ambulate and can result in significant discomfort behind the knee when ambulating over extended distances.

Improvements are clearly needed in Swedish Knee Cage designed knee braces used in the treatment and support of the genu recurvatum.

SUMMARY OF THE INVENTION

The present invention is a significant improvement over typical Swedish Knee Cage brace designs and all others designs known in the prior art. In the improved knee brace of the present invention, an inflatable air bladder is inserted between the rigid bar behind the knee and the patient's knee. The inflatable air bladder provides three significant improvements as well a multitude of other smaller improvements over existing hyperextension brace designs.

First, the patient can inflate or deflate the air bladder to provide optimal support and control of knee movement depending on patient activity without having to make adjustments to the hyperextension bar which usually requires the use of tools and potentially the assistance of a professional fitter, known as an orthotist, or another skilled practioner.

Secondly, comfort is significantly improved with the present knee brace because a considerable amount of force placed onto the back of the knee with each step is absorbed by the air bladders and forces a reactive "push back," which reduces patient exertion.

Thirdly, the reactive "push back" provided by the air bladder facilitates normal gait biomechanics thereby improving patient gait with less expenditure of energy, greater step and stride length and a reduction in postural trunk adjustments to "unload" the knee for lessening the hyperextension moment of the knee joint.

Further, the use of an adjustable inflatable air bladder positioned between the hyperextension stop component of the knee brace and the patient's leg creates a dynamic brace as opposed to a static one. The inflated air bladder will absorb the hyperextension moment of the knee joint and push back behind the knee as the air bladder returns to its inflated shape. This absorption significantly improves comfort for the patient because the posterior movement of the knee joint is absorbed as the air bladder is compressed. The reactive "push back" of the air bladder to its inflated shape also provides a dynamic forward movement of the knee joint to facilitate a more normal knee movement by converting the posterior movement into an anterior movement force. Instead of a static block, the brace becomes a dynamic assist in controlling and reversing hyperextension of the knee, which a static block cannot do. The "halting" gait of a static hyperextension block design, as seen in the prior art, is therefore significantly reduced and the use of inflatable air bladder instead leads to improvements in gait and as well less energy expenditure by the patient to ambulate. As a result, the patient's step length improves. Further, the balance of time spent on each leg during gait improves resulting in a more balanced gait for the person suffering from genu recurvatum.

These objects of the invention and others will be further shown and understood by taking into account the figures along with the detailed description and the claims all set forth herein below.

BRIEF DESCRIPTION OF THE DRAWINGS

The detailed description of the invention, contained herein below, may be better understood when accompanied by a brief description of the drawings, wherein.

DETAILED DESCRIPTION OF THE PREFERRED EMBODIMENT

Figure 1:
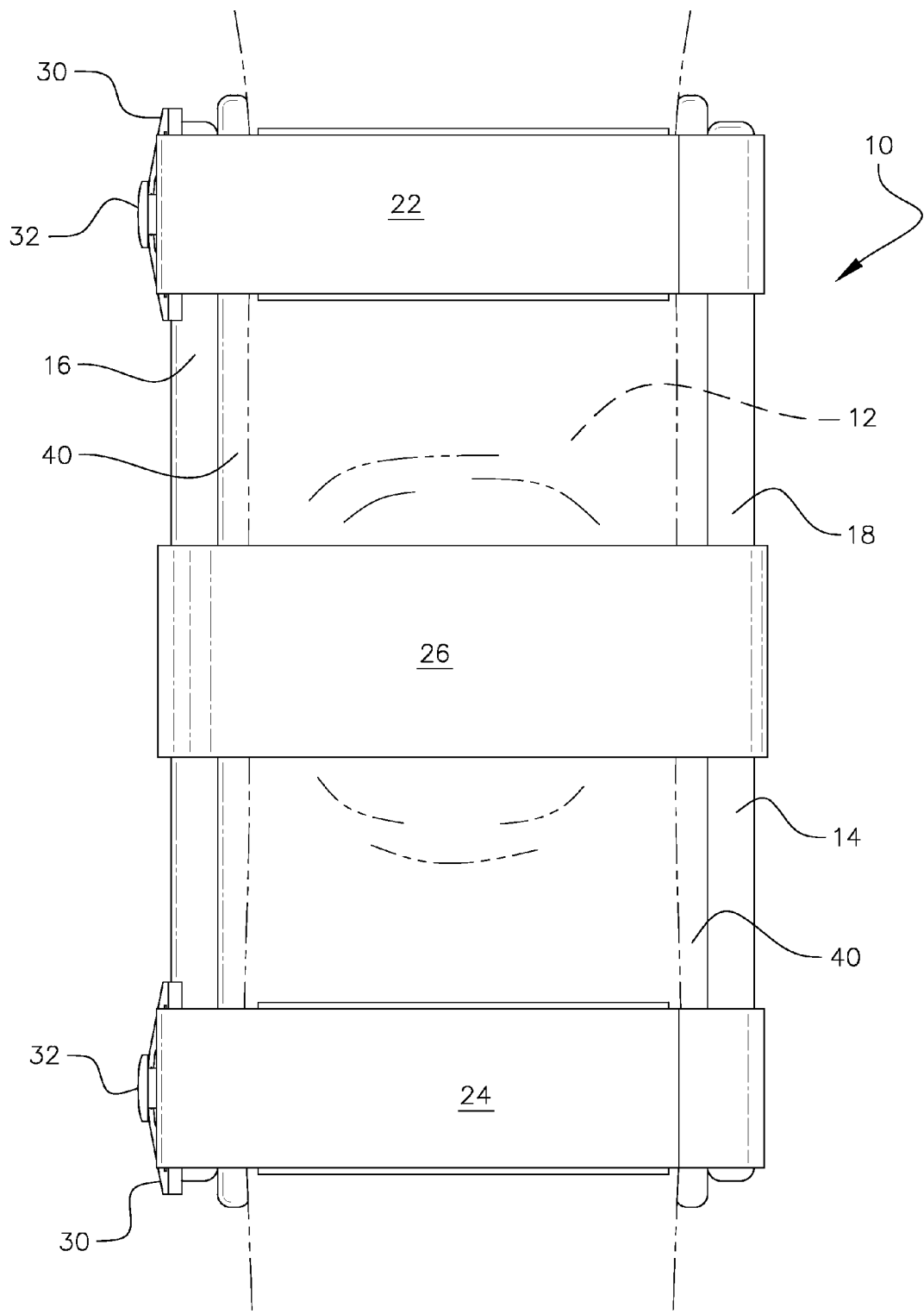
FIG. 1 is a front elevational view of the novel hyperextension knee brace of the present invention shown to be employed on a knee of a patient suffering from genu recurvatum.

Throughout the following detailed description, the same reference numerals refer to the same elements in all figures.

Referring to FIGS. 1-8, a preferred hyperextension knee brace 10 of the present invention is shown. FIG. 1 illustrates how brace 10 is employed on a knee 12 of a patient suffering from genu recurvatum.

Figure 7:
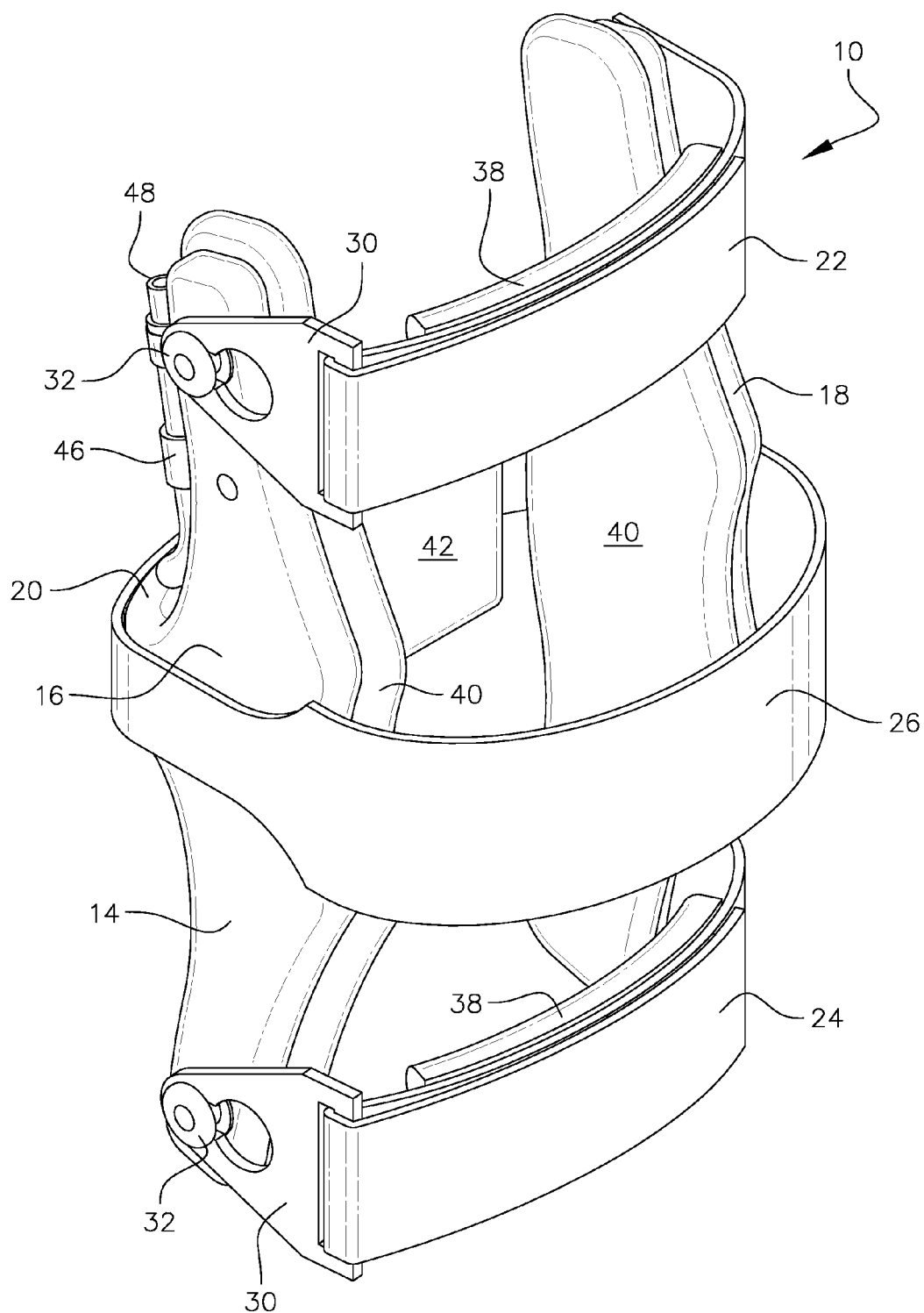
FIG. 7 is a front perspective view of the hyperextension knee brace of the present invention.
Figure 8:
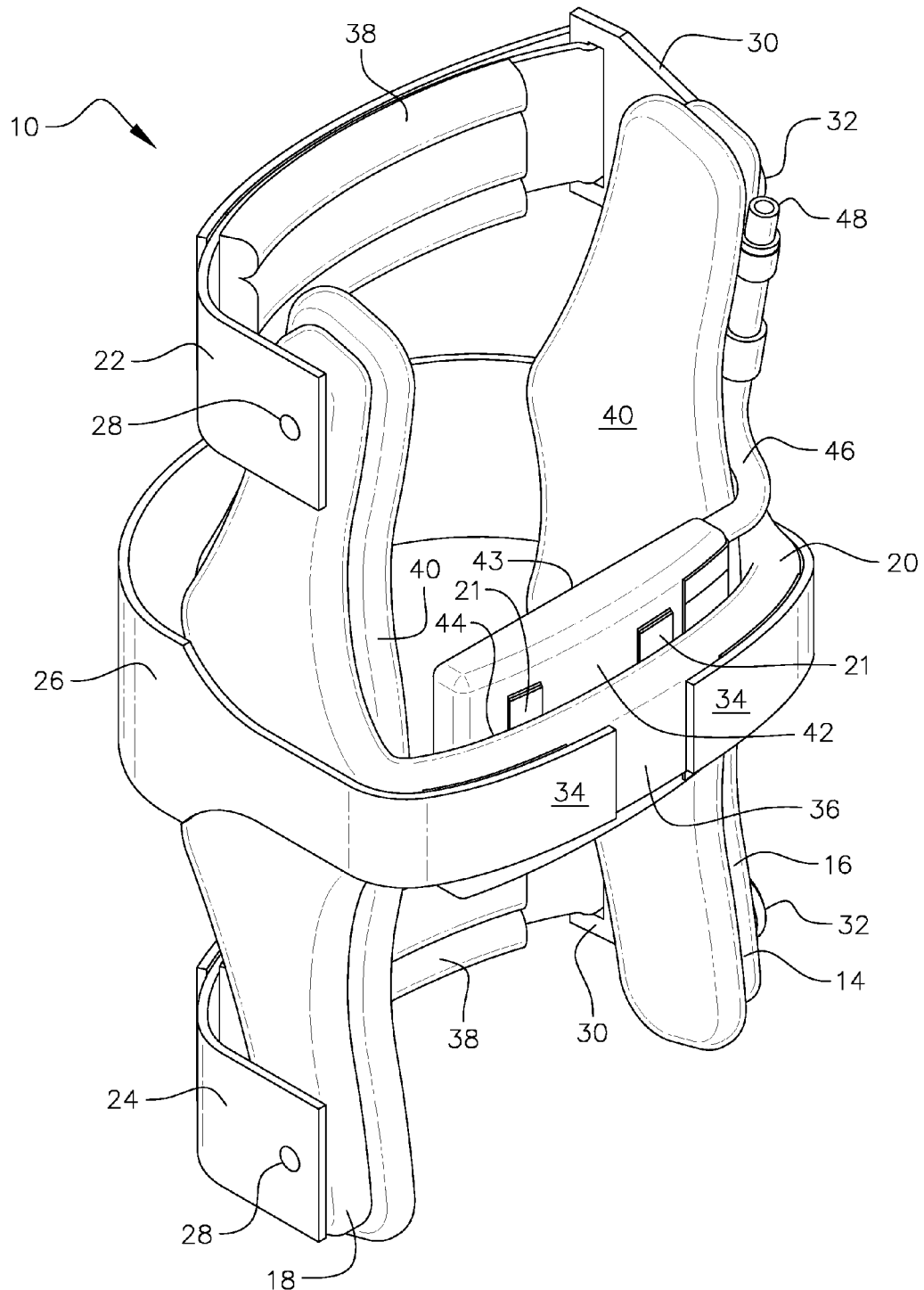
FIG. 8 is a rear perspective view of the novel hyperextension knee brace of the present invention.

Referring now to FIGS. 7 and 8, it is shown that brace 10 includes a frame member 14 that includes a left lateral upright 16 and a right lateral upright 18 and an integral horizontally disposed back support 20 connecting the left and right lateral uprights 16 and 18, respectively. In the preferred embodiment, frame member 14 is constructed from a rigid material. However, in alternate embodiments, frame member 14 can be made from either a semi-rigid material or from a soft pliable kind, which can provide dynamic conformability. Further, as indicated above, in the preferred embodiment, back support 20 is integral with frame member left and right lateral uprights, 16 and 18. However, in alternate embodiments, back support 20 can be non-integrally attached by any known means of attachment. Further, it is shown that both left and right lateral uprights, 16 and 18, have a unique shape that provides a bulging center portion at the area where the inside portion of the uprights positioned against the knee and upper and lower ends, which angle slightly backwardly. However, nothing herein limits other shapes and angles to be used with lateral uprights, 16 and 18.

With continuing reference to FIGS. 7 and 8, it is shown that brace 10 has a plurality of strapping and in particular, a thigh strap 22, a shin strap 24 and a patella strap 26 all of which are disposed, in a preferred embodiment, on an anterior side of brace 10. However, in alternate embodiments, thigh and shin strap, 22 and 24, can be posteriorly disposed, or alternated such that one of such straps is anteriorly disposed while the other is posteriorly disposed. Straps 22, 24 and 26 are all made from a pliable material such that they can give and take a little when tension is applied and released all the while supplying comfort and support to the patient. However, nothing herein limits the use of any other material that is less pliable than that is used on the preferred embodiment.

Figure 4:
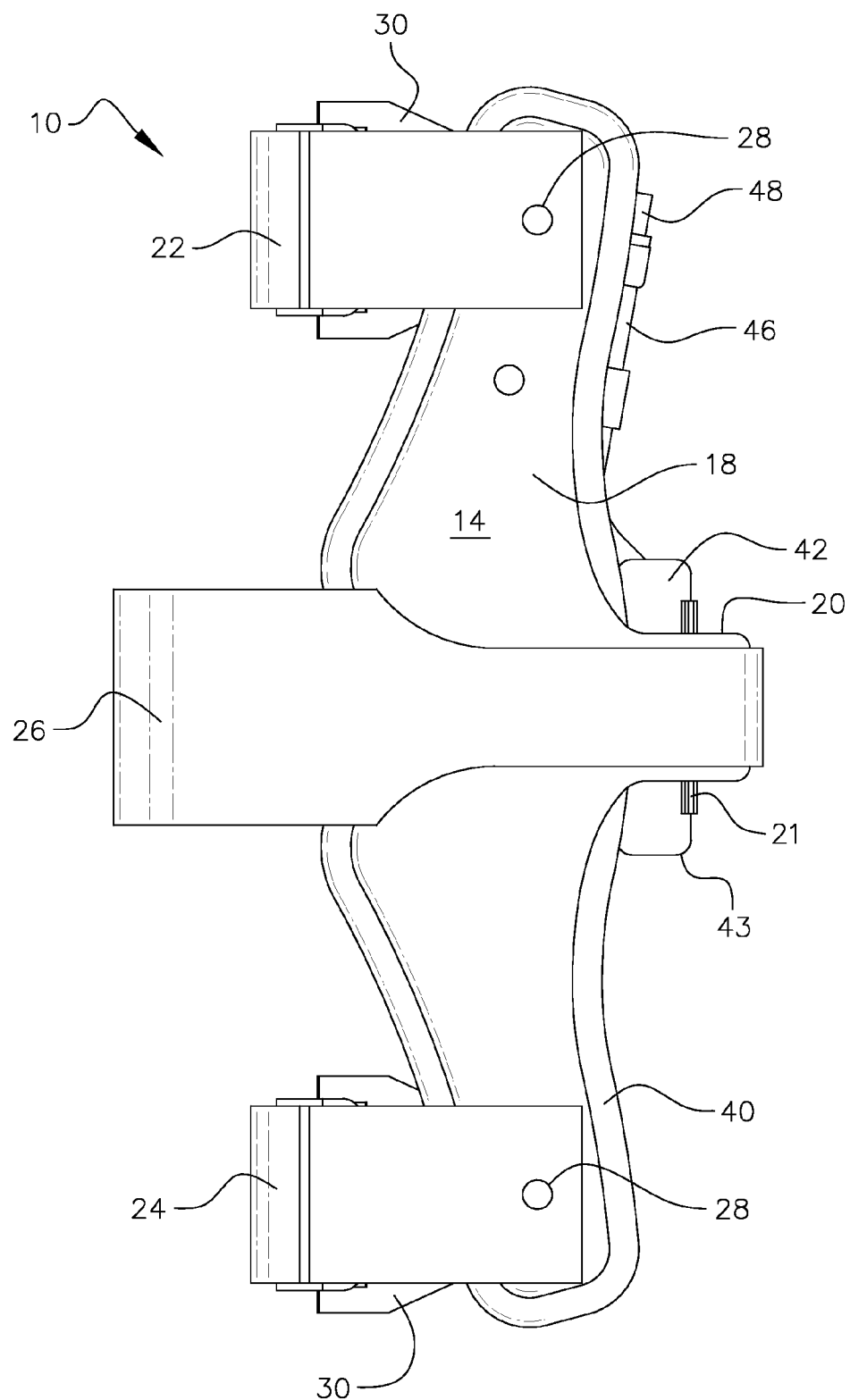
FIG. 4 is a right elevational view of the hyperextension knee brace of the present invention.

As shown in FIG. 4, thigh and shin cuff, 22 and 24, are attached to frame member 14 on one end on right lateral upright 18 by rivets 28. Whereas the opposed ends of straps 22 and 24, as seen in FIGS. 1-3 and 5-7 are attached by a quick release mechanism 30 that attaches to an outwardly extending pin 32 fixed to left lateral upright 16. Nothing herein limits the reverse configuration wherein the rivets 28 are disposed on left lateral upright 16 and the quick release mechanisms 30 and the pins 32 are located on right lateral upright 18.

Figure 2:
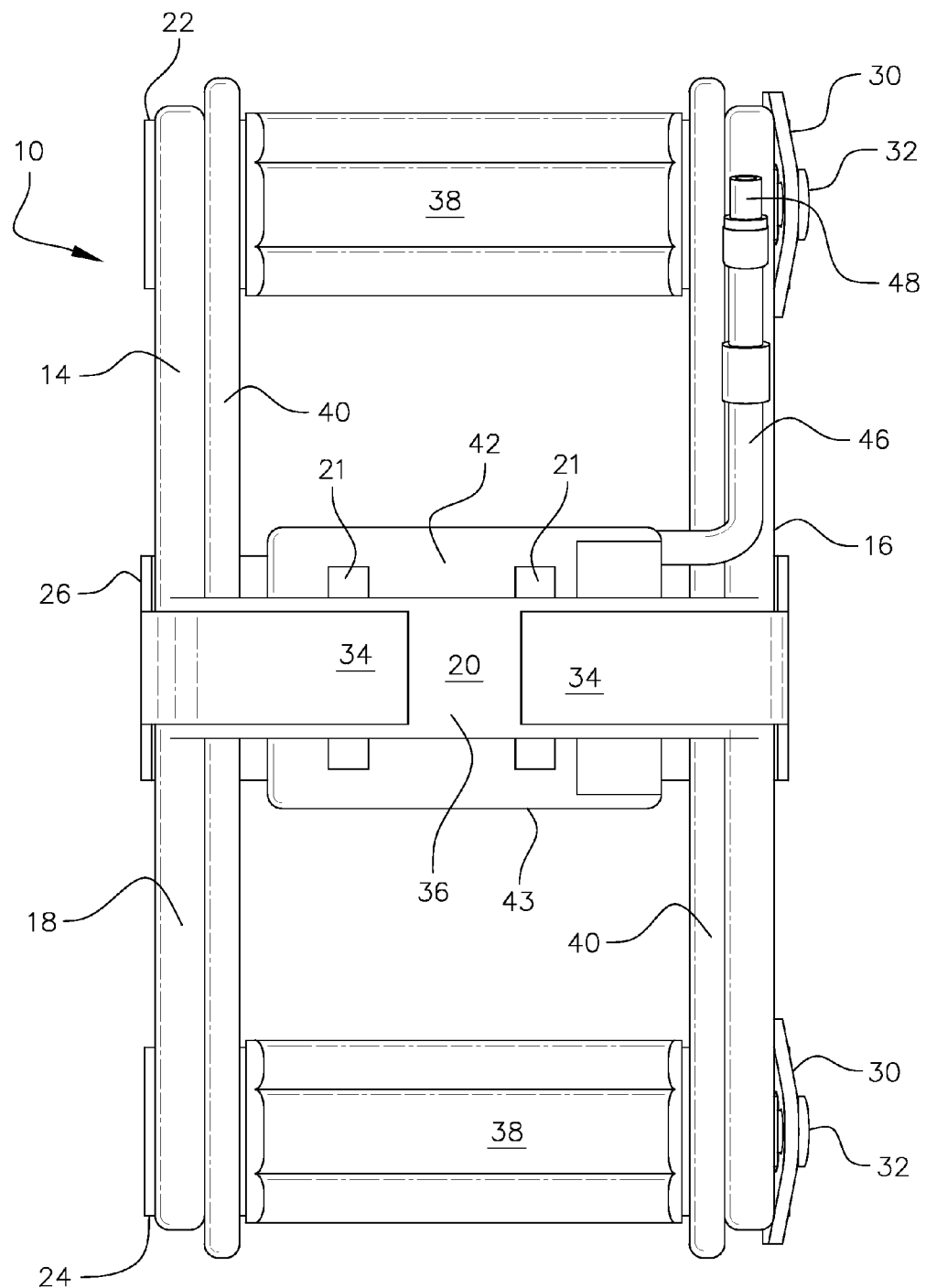
FIG. 2 is a rear elevational view of the hyperextension knee brace of the present invention.
Figure 3:
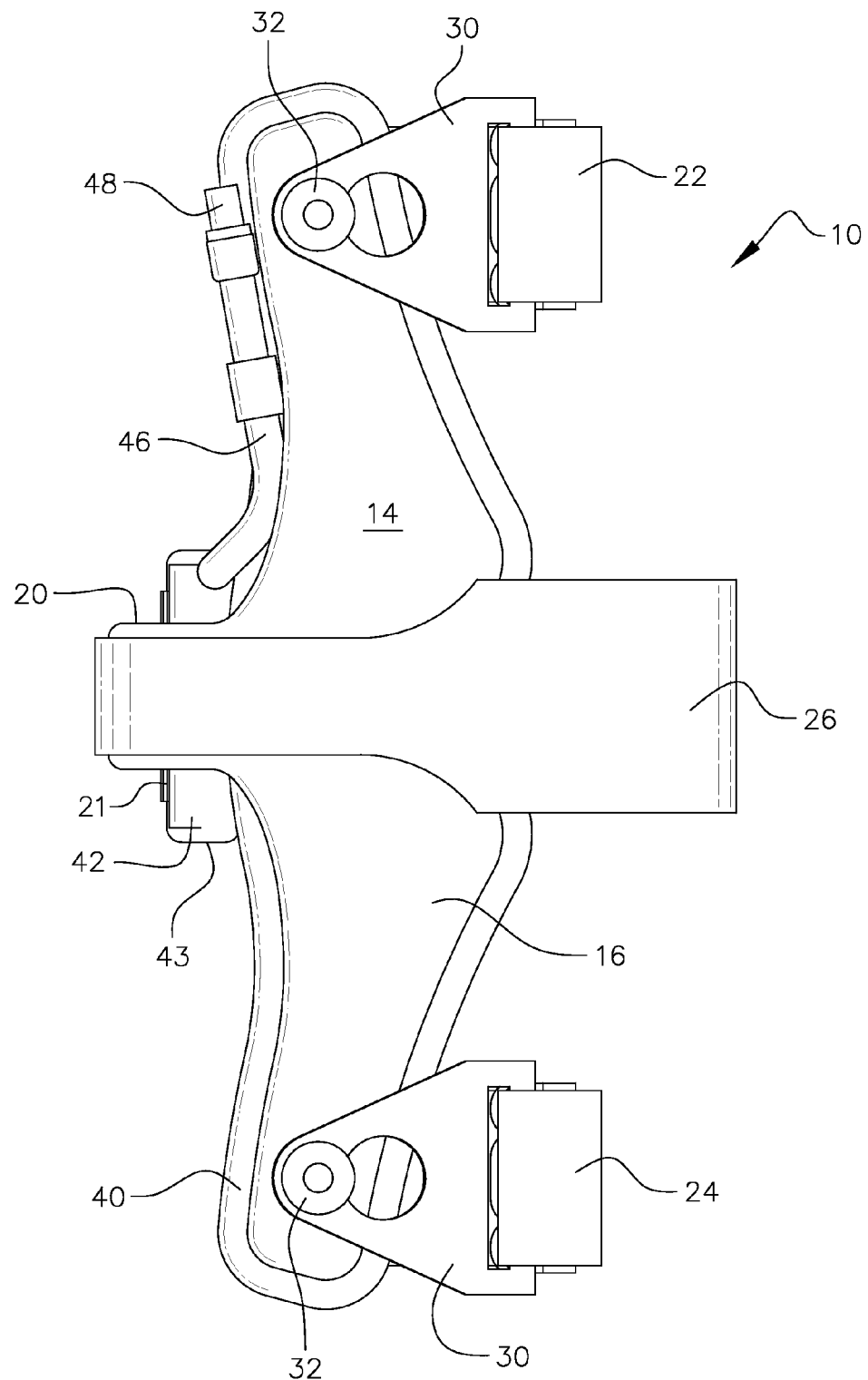
FIG. 3 is a left elevational view of the hyperextension knee brace of the present invention.
Figure 5:
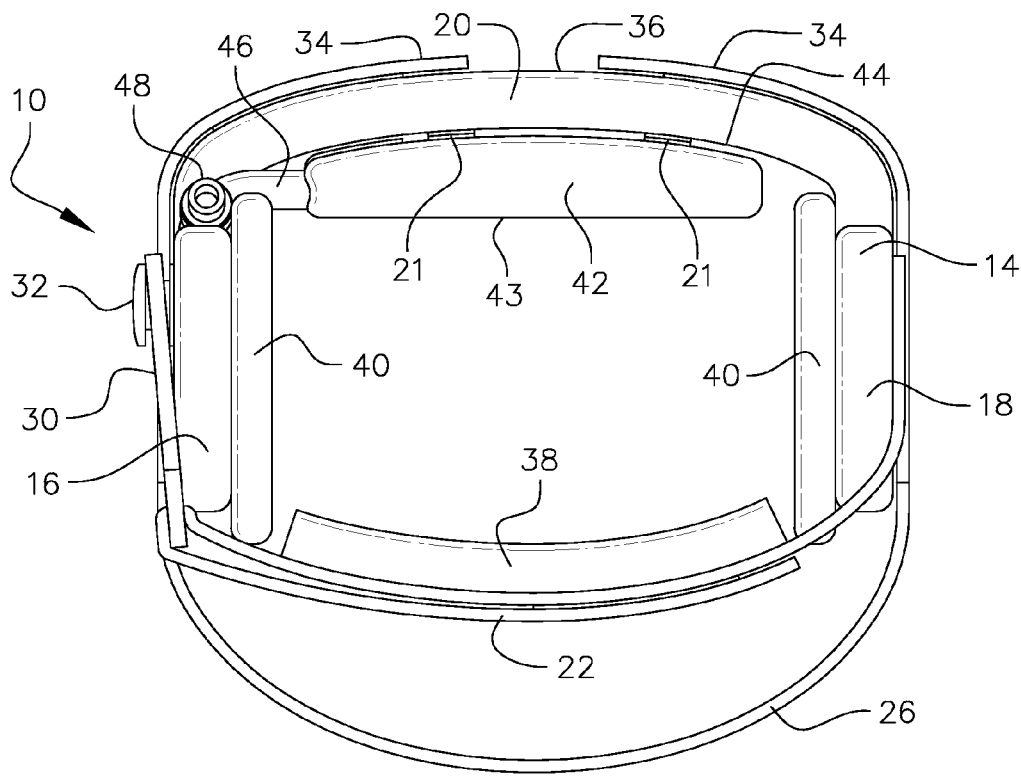
FIG. 5 is a top plan view of the hyperextension knee brace of the present invention.
Figure 6:
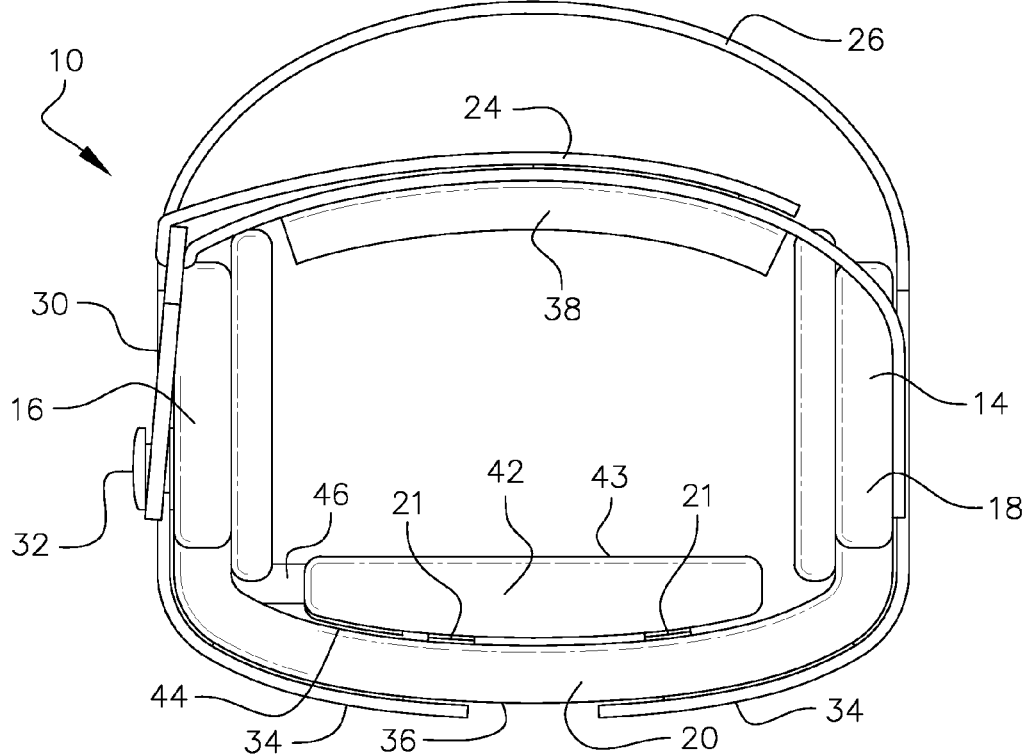
FIG. 6 is a bottom plan view of the hyperextension knee brace of the present invention.

As best shown in FIGS. 2 and 8, patella strap 26 has two opposed ends 34, which have disposed on an inner surface (not shown) hook and loop material, which then mates with reciprocating hook and loop material (also not shown) on a outer surface 36 of back support 20 (see FIGS. 5 and 6). It is understood that the preferred embodiment for patella strap 26 has been described as attaching to back support 20 by hook and loop material. However, nothing herein limits other means of attachment including a quick release mechanism like that employed with thigh and shin straps 22 and 24. And for that matter, nothing herein limits thigh and shin straps 22 and 24 from being attached by hook and look material or other known attachment means.

With reference again to FIGS. 7 and 8, and with further reference to FIG. 2, it is shown that brace 10 has a pair of cushioning pads 38, disposed along inner surfaces of thigh and shin straps 22 and 24 to provide extra comfort and secure fitting to the leg of the patient, and to also minimize, if not eliminate, brace migration (i.e., brace slippage) during ambulation or leg extension and contraction. Further, as also shown in FIGS. 7 and 8, as well as FIGS. 1, 2, 5 and 6, left and right lateral uprights, 16 and 18, both have disposed upon inner surfaces thereupon a cushion pad 40 for again providing extra comfort and to provide a secure fitting to the leg of the patient, and to minimize, or eliminate, brace migration during ambulation and leg extension and contraction.

With reference now to FIGS. 2-8, an inflatable air bladder 42 is provided along an inner surface 44 of back support 20 (see FIGS. 5 and 6). In the preferred embodiment, reciprocal hook and loop material is used on back support 20 and an outer pouch that surrounds air bladder 42 for maintaining it in place along back support 20. Further shown, is that air bladder 42 has an inflation tube 46 with an end portion 48 by which an inflation device, such as an bulbous pump (not shown), can be used to inflate or deflate the air bladder as needed to provide the proper amount of reactive "push back" force needed to treat a hyper extended knee joint of a patient.

Equivalent elements as described hereinabove can be substituted for the ones set forth herein to achieve the same results in the same manner and in the same way.

Having thus described the novel and non-obvious invention herein, what is desired to be obtained through Letters Patent is:

1. A knee brace for treating hypertension of a knee in a patient, the knee brace comprising:
   a) a pair of vertical lateral uprights;
   b) a back support member positioned horizontally to and at a generally middle portion of the pair of vertical lateral uprights and extending backwardly from a front portion of the knee brace, the pair of vertical lateral uprights and the back support member defining a frame member of the knee brace;
   c) a thigh strap and a shin strap connected at opposed ends thereof to the frame member;
   d) a plurality of cushion pads disposed along inner surfaces of the pair of vertical lateral uprights and the thigh and shin straps; and e) an inflatable air bladder positioned along an inner surface of the back support member for positioning behind the knee when the knee brace is employed on the patient, the air bladder having an inflation tube for increasing or decreasing the air volume within the air bladder to affect a range of motion for the patient's knee.

2. The knee brace of claim 1, wherein the pair of vertical lateral uprights are constructed from a material that provides for varying degrees of rigidity chosen from the group consisting of rigid, semi-rigid and flexible.

3. The knee brace of claim 1, wherein the pair of vertical lateral uprights comprises a left and right lateral upright and the back support is integrally formed attached to said left and right lateral uprights such that the frame member has a single integral construction.

4. The knee brace of claim 1, wherein the pair of vertical lateral uprights comprises a left and right lateral upright and the back support member is removeably attached to said left and right lateral uprights.

5. The knee brace of claim 1, further comprising a patella strap attached at opposed ends to the frame member back support member such that the patella strap extends around the front portion of the knee brace.

6. The knee brace of claim 5, wherein the patella strap has opposed ends for securing to an outer surface of the back support member by a hook and loop material.

7. The knee brace of claim 1, wherein the thigh and shin straps are each attached at one end by a rivet to one of the pair of vertical lateral uprights and on an opposed end attached to the other one of the pair of vertical lateral uprights by a quick release mechanism.

8. The knee brace of claim 1, wherein the thigh and shin straps extend around the front portion of the knee brace.

9. The knee brace of claim 1, wherein the plurality of cushion pads comprises a first adjustable cushion pad located along an inner surface of the thigh strap and a second adjustable cushion pad located along an inner surface of the shin strap.

10. The knee brace of claim 1, wherein the plurality of cushion pads comprises a pair of vertically disposed pads attached along inner surfaces of the pair of vertical lateral uprights.

11. The knee brace of claim 1, wherein the air bladder is inserted within a pouch, the pouch having hook loop material attached to a back wall of said pouch for mating to reciprocal hook and loop material positioned along the inner surface of the back support member.

12. The knee brace of claim 1, wherein the pair of vertical lateral uprights both have top and bottom ends that extend backwardly in relation to an upright side axis.

13. The knee brace of claim 12, wherein both lateral upright top and bottom ends extend backwardly at equal distances.

* * * * *